US011000651B2

(12) United States Patent
Anderson et al.

(10) Patent No.: US 11,000,651 B2
(45) Date of Patent: May 11, 2021

(54) SPRING DRIVEN INJECTOR APPARATUS WITH NEEDLE INSERTION

(71) Applicant: Owen Mumford Limited, Oxford (GB)

(72) Inventors: Oliver Anderson, Oxford (GB); Toby Cowe, Oxford (GB); Andrew Varde, Ringwood (GB); Jeremy Marshall, Oxford (GB)

(73) Assignee: Owen Mumford Limited, Oxford (GB)

( * ) Notice: Subject to any disclaimer, the term of this patent is extended or adjusted under 35 U.S.C. 154(b) by 1053 days.

(21) Appl. No.: 15/117,596

(22) PCT Filed: Feb. 10, 2015

(86) PCT No.: PCT/GB2015/050367
§ 371 (c)(1),
(2) Date: Aug. 9, 2016

(87) PCT Pub. No.: WO2015/118358
PCT Pub. Date: Aug. 13, 2015

(65) Prior Publication Data
US 2016/0354553 A1 Dec. 8, 2016

(30) Foreign Application Priority Data
Feb. 10, 2014 (GB) .................................. 1402261

(51) Int. Cl.
*A61M 5/32* (2006.01)
*A61M 5/19* (2006.01)
(Continued)

(52) U.S. Cl.
CPC ........ *A61M 5/3287* (2013.01); *A61M 5/1454* (2013.01); *A61M 5/14248* (2013.01);
(Continued)

(58) Field of Classification Search
CPC ...... A61M 5/3287; A61M 2005/14252; A61M 5/3298; A61M 5/14248;
(Continued)

(56) References Cited

U.S. PATENT DOCUMENTS 5,609,577 A 3/1997 Haber et al.
5,846,225 A * 12/1998 Rosengart .............. A61K 48/00
604/115
(Continued)

FOREIGN PATENT DOCUMENTS

EP 0014006 A2 10/2012
WO 97/21457 A1 6/1997
(Continued)

OTHER PUBLICATIONS

International Search Report and Written Opinion of the International Searching Authority issued in PCT application No. PCT/GB2015/053067, dated Jul. 15, 2015, 19 pages.
(Continued)

*Primary Examiner* — Nathan R Price
*Assistant Examiner* — Melissa A Snyder
(74) *Attorney, Agent, or Firm* — Quarles & Brady LLP

(57) ABSTRACT

An injection device is disclosed which comprises a housing (140, 240, 440, 740) for a plurality of cartridges (110,310, 410,810) each containing a medicament to be administered to a patient. A plurality of needles (120, 220, 320, 420, 720, 820) may be provided in communication with the plurality of cartridges. A delivery mechanism is arranged to deliver medicament through the plurality of cartridges via the plurality of needles. An injection device may comprise a drive member (130) having a cam surface (136) configured to engage a surface of a carrier (150) and rotate the carrier about a pivot (152) and at least one plunger (134) arranged to engage a cylinder in the cartridge.

6 Claims, 8 Drawing Sheets

(51) Int. Cl.
*A61M 5/42* (2006.01)
*A61M 5/142* (2006.01)
*A61M 5/145* (2006.01)
*A61M 5/20* (2006.01)
*A61M 5/315* (2006.01)
*A61M 5/158* (2006.01)

(52) U.S. Cl.
CPC .......... *A61M 5/19* (2013.01); *A61M 5/2033* (2013.01); *A61M 5/31578* (2013.01); *A61M 5/3202* (2013.01); *A61M 5/3298* (2013.01); *A61M 5/422* (2013.01); *A61M 2005/14252* (2013.01); *A61M 2005/14256* (2013.01); *A61M 2005/1581* (2013.01); *A61M 2005/206* (2013.01); *A61M 2005/3289* (2013.01)

(58) Field of Classification Search
CPC ...... A61M 2005/14284; A61M 5/1452; A61M 2005/14533; A61M 5/1454; A61M 5/19; A61M 5/2033; A61M 5/31578

See application file for complete search history.

(56) References Cited

U.S. PATENT DOCUMENTS

| | | | |
|---|---|---|---|
| 5,858,001 A * | 1/1999 | Tsals | A61M 5/14248 604/135 |
| 5,865,804 A | 2/1999 | Bachynsky | |
| 6,149,626 A | 11/2000 | Bachynsky et al. | |
| 2004/0116847 A1* | 6/2004 | Wall | A61K 9/0019 604/93.01 |
| 2005/0203461 A1* | 9/2005 | Flaherty | A61M 5/14248 604/131 |
| 2013/0345638 A1 | 12/2013 | Heidendreich | |

FOREIGN PATENT DOCUMENTS

| | | |
|---|---|---|
| WO | 2005/056077 A2 | 6/2005 |
| WO | 2011/014514 A1 | 2/2011 |
| WO | 2012/145752 A2 | 10/2012 |

OTHER PUBLICATIONS

British Search Report issued in GB 1402261.0, searched Aug. 12, 2014, 2 pages.

"Communication pursuant to Rule 164(2)(b) and Article 94(3) EPC", European Application No. 15708029.2, dated Dec. 12, 2017, 8 pages.

* cited by examiner ating from the plurality of cartridges via the plurality of needles.

SPRING DRIVEN INJECTOR APPARATUS WITH NEEDLE INSERTION

CROSS-REFERENCE TO RELATED APPLICATIONS

This application represents the U.S. National Stage of International Application No. PCT/GB2015/050367 filed Feb. 10, 2015, which is incorporated by reference in its entirety and is based on, claims priority to, and incorporates herein by reference in its entirety, British Patent Application Serial No. GB 1402261.0, filed Feb. 10, 2014, and entitled, "Spring Driven Injector Apparatus with Needle Insertion."

FIELD OF THE INVENTION

This invention relates to an injection apparatus and in particular, but not exclusively, to an injection apparatus arranged to be worn against the skin of a user.

BACKGROUND OF THE INVENTION

Injection devices, such as the Owen Mumford Autopen®, are commonly used by patients to self-administer injections of medicament. Such devices are typically provided in a pen-like body which contains, defines or receives a cartridge (which it will be understood may comprise a syringe) of medicament. The injection device generally comprises a delivery mechanism which is arranged to dispense the medicament via a needle in response to a user pressing a button or trigger. Depending upon the type of device and or medicament to be delivered the injection device may be arranged to deliver the entire contents of the cartridge or a selected dose therefrom. In some injection devices the delivery mechanism may also be arranged to move the needle between a retracted and delivery position and, in doing so, may automatically pierce the skin of the user prior to the dispensing of the medicament.

In some circumstances it is necessary to deliver medicaments in relatively high volumes (for example up to 10 mL of medicament in a single dose) and/or to deliver medicament which are highly viscous such that it may be necessary for the delivery to be carried out over an extended period. Such injections may normally necessitate a user remaining in a health care facility for the duration of an injection. As an alternative, it would be advantageous to provide an injector device which a user could wear against the skin during the delivery of a dose (which could for example take an hour), and such devices may be referred to as "bolus injectors". Such bolus injector devices are distinct from other wearable devices such as infusion pumps (for example for use in the treatment of diabetics) which are generally more complex and expensive devices which are arranged to deliver a regular discrete dose of medicament with a pre-defined time interval or with a user controlled dosage.

Embodiments of the invention are intended to provide an injection device which may be used as a wearable or bolus injector.

SUMMARY OF THE INVENTION

According to one aspect of the invention, there is provided an injection device comprising: a housing for a plurality of cartridges each containing a medicament to be administered to a patient; a plurality of needles in communication with the plurality of cartridges; and a delivery mechanism arranged to deliver medicament through the plurality of cartridges via the plurality of needles.

Arrangements in accordance with embodiments of the invention are particularly advantageous for high volume and/or high viscosity medicaments. In the case of high volume injections the medicament can be delivered in several neighbouring locations to allow faster medicament dissipation while avoiding or minimising the risk of a bolus forming. In the case of high viscosity injections, the plurality of needles provide a larger flow path and may reduce the drug delivery rate through each needle so as to reduce the pressure build up in the cartridge.

The delivery of medicament from the plurality of cartridges may be arranged to be simultaneous (or at least substantially simultaneous). For example, whilst there may be some nominal delay or overlap in the delivery, a bolus injector may not generally be intended to provide a sequence of distinct/separate injections from the plurality of cartridges.

The plurality of cartridges may have an elongate shape. The cartridges may be syringes. In some embodiments the cartridges may be formed as part of the injector. However, it may be convenient to provide a device which is adapted to receive standard cartridges which may be readily available pre-filled with the desired medicament. The longitudinal axis of the cartridges is generally aligned with a longitudinal axis of the housing. Typically the longitudinal axis of the cartridges each extends parallel to the longitudinal axis of the housing. The plurality of cartridges are typically arranged in a side-by-side arrangement.

The plurality of needles extend in a direction which is non-parallel with the longitudinal axis of the housing. The needle may be moveable and, therefore, the needle may extend in said non-parallel direction in at least a delivery position of the needle. For example, the needles may extend in a direction which is substantially perpendicular to the longitudinal axis of the housing.

The delivery mechanism may be arranged to move the plurality of needles between a retracted position and a delivery position. The needles may extend substantially perpendicularly to the longitudinal direction of the housing in at least the delivery position. The delivery mechanism may move the needles simultaneously.

The movement of the needles (by the delivery mechanism) displaces the tips of the needles from a retracted position to a delivery position. In the retracted position the tips of the needles lay between upper and lower planes of the housing. In the delivery position the tips are positioned beyond the lower plane of the housing. It will be appreciated that the lower plane of the housing will typically be aligned with the skin of the user in use and, therefore, by moving beyond the plane the tip of the needle may pierce the skin.

The injection device may further comprise a carrier moveably mounted within said housing and arranged to carry the plurality of needles. The delivery mechanism may be arranged to move the carrier between an initial position and delivery position. It will be appreciated that the initial position may correspond to the retracted position of the needles and the delivery position may correspond to the delivery position of the needles. The carrier may also carry the plurality of cartridges.

The carrier may be generally moveable in a direction toward the lower (skin facing) surface of the housing. The carrier may be linearly moveable relative to the housing. For example the carrier may be linearly moveable in a transverse direction relative to the housing. The carrier may be rotatable relative to the housing. The carrier may be pivotally connected to the housing. The pivotal connection may be proximal to a rearward end of the carrier. The needle(s) may be provided proximal to a forward end of the carrier.

The delivery mechanism may comprise a drive member longitudinally moveable relative to the housing and a stored energy element arranged to drive the drive member in the longitudinal direction upon activation of the injection device. The drive member may comprise a cam surface configured to engage a surface of the carrier and rotate the carrier about a pivot. The drive member may comprise a single drive member or may comprise a drive member associated with each cartridge. Equally it will be appreciated that the stored energy element may comprise a plurality of elements (for example one associated with each cartridge.

The (or each) drive member may further comprise a plurality of plunger members arranged to engage a cylinder in each of the plurality cartridges.

According to another aspect of the invention, there is provided an injection device comprising: a carrier pivotally mounted within a housing for at least one cartridge containing a medicament to be administered to a patient; a needle fixed relative to the carrier and extending forwardly to a tip in a direction which is non-parallel with the longitudinal axis of the cartridge such that rotation of the cartridge body relative to the housing may provide a penetration movement of the needle; and a delivery mechanism comprising: a drive member longitudinally moveable relative to the housing; a stored energy element arranged to drive the drive member upon activation of the injection device; and wherein the drive member comprises a cam surface configured to engage a surface of the carrier and rotate the carrier about a pivot and at least one plunger arranged to engage a cylinder in the cartridge.

The cartridge may be integrally formed with the carrier or the cartridge may be a discrete component (for example a standard syringe or cartridge).

The drive member may be configured such that the pivoting movement of the carrier, as a result of engagement of the cam surface, moves the needle(s) to a delivery position. The drive member may be configured such that the pivoting movement of the carrier occurs prior to the plunger members engaging the cartridge(s). For example the pivoting movement of the carrier may bring the plunger members into alignment with the cartridge.

The drive member may be releasably coupled to the stored energy element. The drive member may be uncoupled by movement in a direction transverse to the actuation direction.

According to a further aspect of the invention there is provided an injection device comprising: at least one cartridge containing a medicament to be administered to a patient; a drive member, moveable in a longitudinal direction relative to the cartridge to deliver a dose of medicament therefrom; and a stored energy element arranged to move the drive member during delivery; wherein the drive member is releasably coupled to the stored energy source and may be decoupled by movement in a direction transverse to the actuation direction.

The housing may be arranged such that transverse movement of the drive member is restrained until the drive member has completed delivery of the medicament, for example when the drive member reaches a forwardmost position. It will be appreciated that in the forwardmost position a full dose of medicament has generally been dispensed from the cartridge.

The transverse movement of the drive member may also move the carrier. Thus, the decoupling may provide a retraction movement of the needle(s). A retraction biasing member may be arranged to urge the drive member (or carrier) towards the retracted position.

The delivery mechanism may comprise: a plunger having a forward end extending into the cartridge for expressing a dose in use and a rearward end including a profiled head. A biasing means may be provided to urge the plunger towards its forward position. A guide plate may be fixed relative to the housing and have a guide slot for receiving the profiled head of the plunger to latch the plunger in a rearward position against the bias of the biasing means. Movement of the carrier from the initial position to the delivery position may translate the plunger head along the guide slot to an opening aligned with the delivery position such that the profiled head is released from the slot and may be driven forwardly by the biasing means.

The opening in the guide slot may be a keyway matching the shape of the plunger head. Alternatively the opening may be a portion of the guide slot having an increased width. Alternatively, the opening may be an open end of the slot which the head may translate beyond.

The guide plate may be arcuate (for example in embodiments in which the carrier is pivotable).

The guide plate may extend substantially perpendicularly to the longitudinal axis of the cartridge (for example in embodiments in which the carrier is linearly moveable)

The delivery mechanism may comprise: a plunger having a forward end extending into the cartridge for expressing a dose in use and a rearward end including a profiled head; a biasing element arranged to urge the plunger towards it forward position; a latch plate fixed relative to the housing and having a slot arranged to receive the profiled head of the plunger and retain the plunger in a rearward position against the force of the biasing element. The delivery mechanism may be actuated in a transverse direction relative to the housing to move the needle in the transverse direction to the delivery position, and release the plunger from the latch plate such that the biasing element may urge the plunger forward in the longitudinal direction.

According to a further aspect of the invention there is provided an injection device comprising a housing for at least one cartridge containing a medicament to be administered to a patient; at least one needle mounted within the housing and extending forwardly, in a direction which is non-parallel to the longitudinal axis of the cartridge, from a rear end associated with the at least one cartridge to a tip, wherein the needle is moveable relative to the housing between a retracted position and a delivery position in which the tip of the needle is displaced by a distance in a direction transverse to the housing; and a delivery mechanism configured to move the needle between said retracted and delivery positions and to dispense medicament from the at least one cartridge, the delivery mechanism comprising: a plunger having a forward end extending into the cartridge for expressing a dose in use and a rearward end including a profiled head; a biasing element arranged to urge the plunger towards it forward position; a latch plate fixed relative to the housing and having a slot arranged to receive the profiled head of the plunger and retain the plunger in a rearward position against the force of the biasing element; and wherein the delivery mechanism is actuated in a transverse direction relative to the housing, moving the needle to the delivery position, and releases the plunger from the latch plate such that the biasing element may urge the plunger forward in the longitudinal direction.

The delivery mechanism may include a trigger member arranged to resiliently deflect the profiled head of the plunger to release the plunger from the latch plate. The, or each, cartridge may be fixed relative to the housing. The, or each, needle is connected to the, or each, cartridge by at least one flexible conduit. As such, the needle(s) may be able to move relative to the cartridge. Such an arrangement may enable the profile of the device to be minimised.

The device may further comprise a plate comprising at least one skin stimulating member which is moveable relative to the housing. For example, the plate may comprise a plurality of blunt spikes. The delivery mechanism may be arranged to move the plate into contact with the user's skin prior to the needle reaching the delivery position. The plate may be compressibly mounted relative to the needle (for example to allow a degree of lost motion between the plate and needle). The plate may be connected to the carrier.

The delivery mechanism may be arranged to rotate the plurality of cartridges about their longitudinal axis; a needle associated with each cartridge having a tip which is radially offset from the longitudinal axis of the cartridge and extends forwardly in the radial plane in a direction perpendicular to the radial direction of the offset. The needle may be coupled to the cartridge such that rotation of the cartridge about its axis rotates the needle between a retracted position and a delivery position.

According to a further aspect of the invention there is provided an injection device comprising: at least one cartridge containing a medicament to be administered to a patient and having a longitudinal axis; at least one needle, in communication with the cartridge, having a tip which is radially offset from the longitudinal axis of the cartridge and extends forwardly in the radial plane in a direction perpendicular to the radial direction of the offset; and a delivery mechanism arranged to rotate the plurality of cartridges about their longitudinal axis; and wherein the needle is coupled to the cartridge such that rotation of the cartridge rotates the needle between a retracted position and a delivery position.

The delivery mechanism may comprise a linear moveable plate coupled to an outer surface of each cartridge. The plate may be arranged such that such that movement of the plate rotates the cartridges simultaneously. The plate may be linearly movable in a generally tangential direction with respect to the outer surface of the cartridges. The plate may comprise a toothed plate which engages with complimentary toothed projections on each cartridge.

The needle may comprise a first portion extending in a radial direction from the cartridge and a second portion extending substantially perpendicular to the radial direction. The needle may have a generally arcuate profile in the radial plane.

The device may further comprise a plunger having a forward end extending into the, or each, cartridge for expressing a dose in use and a rearward end including a profiled head. A biasing element may be arranged to urge the plunger towards it forward position. A latch plate may be provided having a keyway arranged to receive the profiled head of the plunger and retain the plunger in a rearward position against the force of the biasing element. Rotation of the cartridge by the delivery mechanism may be arranged to provide relative rotation between the plunger and latch plate and wherein the keyway and profiled head are moved into alignment when the needle is in the delivery position so as to release the plunger (such that the biasing element may urge the plunger forward in the longitudinal direction).

The injector may be configured to be worn, in use, against the skin of a user. The lower surface of the body of the injection device is generally arranged to be worn against the skin (and may, for example, include an adhesive dressing). The housing of the injection device may generally have a low profile housing such that it may be worn unobtrusively. The longitudinal direction of the housing would generally extend parallel to the surface of the skin.

It will be appreciated that embodiments of the invention may be arranged for subcutaneous delivery Whilst the invention has been described above with reference to a number of embodiments and aspects it is to be understood that it includes any inventive combination of the features set out above or in the following description or drawings.

BRIEF DESCRIPTION OF THE DRAWINGS

Specific embodiments of the invention will now be described in detail, by way of example only, and with reference to the accompanying drawings in which.

DETAILED DESCRIPTION OF EMBODIMENTS

Figure 1:
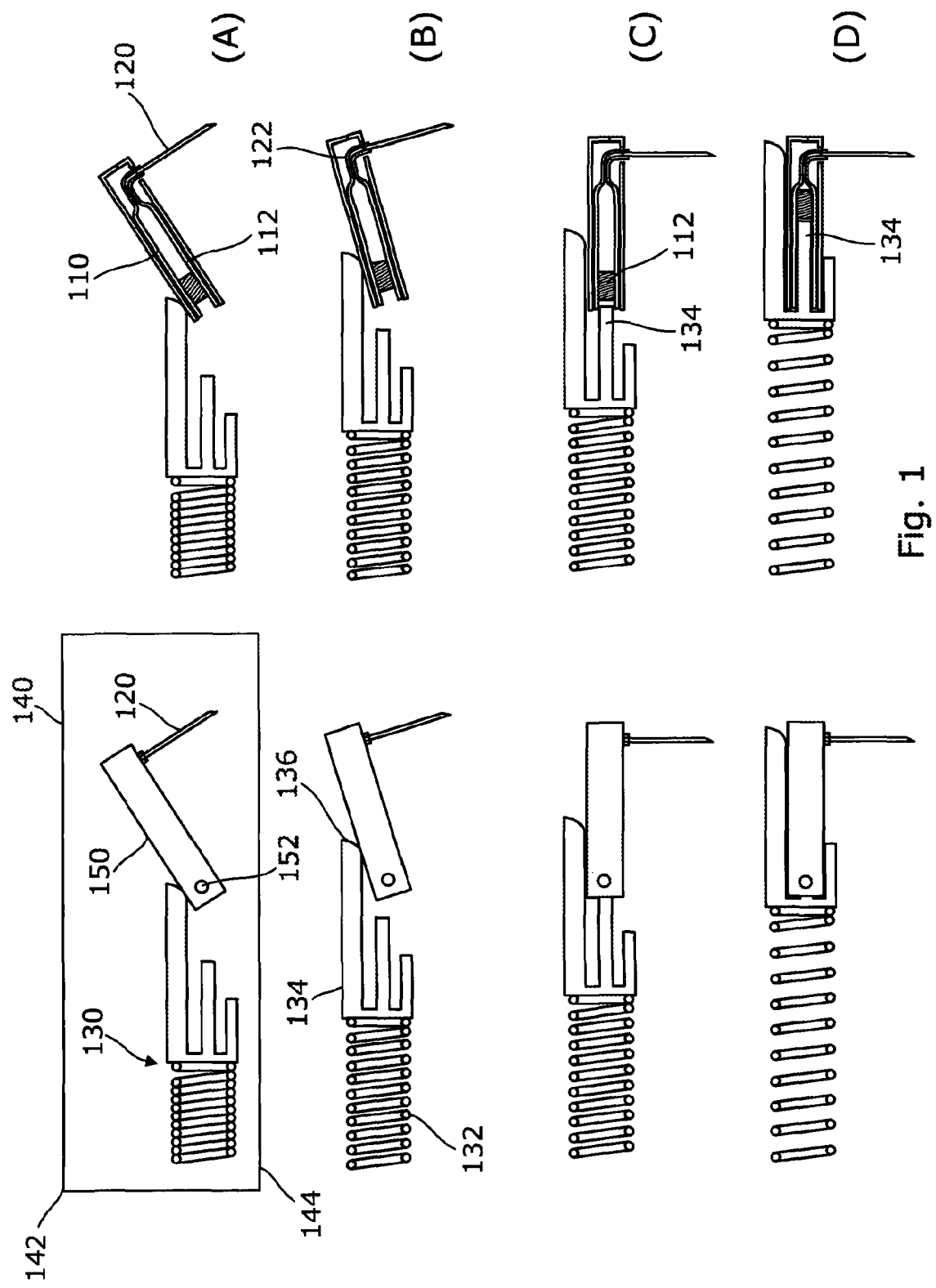
FIG. 1 schematically represents the actuation sequence of an injection device according to a first embodiment of the invention in profile and partial cut away.

A number of embodiments of the invention are described below, it will be noted that in each embodiment the injector device is generally provided with an elongate housing which receives at least one cartridge. The longitudinal axis of the cartridge and housing are generally aligned so as to provide a low profile device. In contrast to conventional pen type injection devices the embodiments all provide an arrangement in which the delivery needle(s) project out of the housing in a transverse direction such that the device may be worn against the skin during medicament delivery.

The disclosed embodiments generally incorporate at least one aspect of the invention. In each embodiment like reference numerals (but with the first digit of the reference numerals is increased in accordance with the figure number) are used for like components for the ease of understanding.

An injection device according to a first embodiment is shown in FIG. 1 and comprises at least one cartridge 110 containing a medicament to be administered to a patient held within a carrier 150 which is pivotally connected at a hinge 152, disposed at a rearward end of the carrier, within a housing 140. At least one needle 120 is provided at the forward end of the carrier and extends in a substantially perpendicular direction to the longitudinal axis of the cartridge 110. Typically the injector comprises a plurality of side-by-side cartridges 110 each associated with a separate needle 120. A curved conduit 122 may be provided between the cartridge 110 and needle 120 to enable the needle to extend at an angle (although it will equally be appreciated that the needle itself could be bent).

A delivery mechanism 130 is provided which comprises a stored energy device, in the form of a coil spring 132, and a drive member 134. The drive member 134 is provided with a forked profile including an upper member having a cam surface 136 which is arranged to act upon the upper face of the carrier 150 during the initial forward movement of the drive member, as shown in FIG. 1(B). Once the carrier 150 has fully pivoted into its delivery position the needle 120 has been moved into a delivery position and it will be noted that the tip of the needle has been displaced downwardly in a direction transverse to the longitudinal axis of the injector beyond the lower plane 144 of the housing 140, as shown in FIG. 1(C). In this position the central plunger 138 of the drive member 134 is aligned with the interior of the cartridge 110 and may continue forward such that it engages the cylinder (or "bung") 112 of the cartridge and urges it forwards to deliver the medicament from the cartridge 110 via the needle 120.

Since the injection device 101 is generally intended for high volume or high viscosity drugs it will be appreciated that embodiments of the invention may be provided with multiple parallel cartridges 110 and needles 120. As such the drive member 134 may be provided with parallel extending plungers 138 which each align with and engage the cylinder 112 of a separate cartridge. Each cartridge may be associated with a separate needle 120 (as seen, for example, in the end view of FIG. 2).

Figure 2:
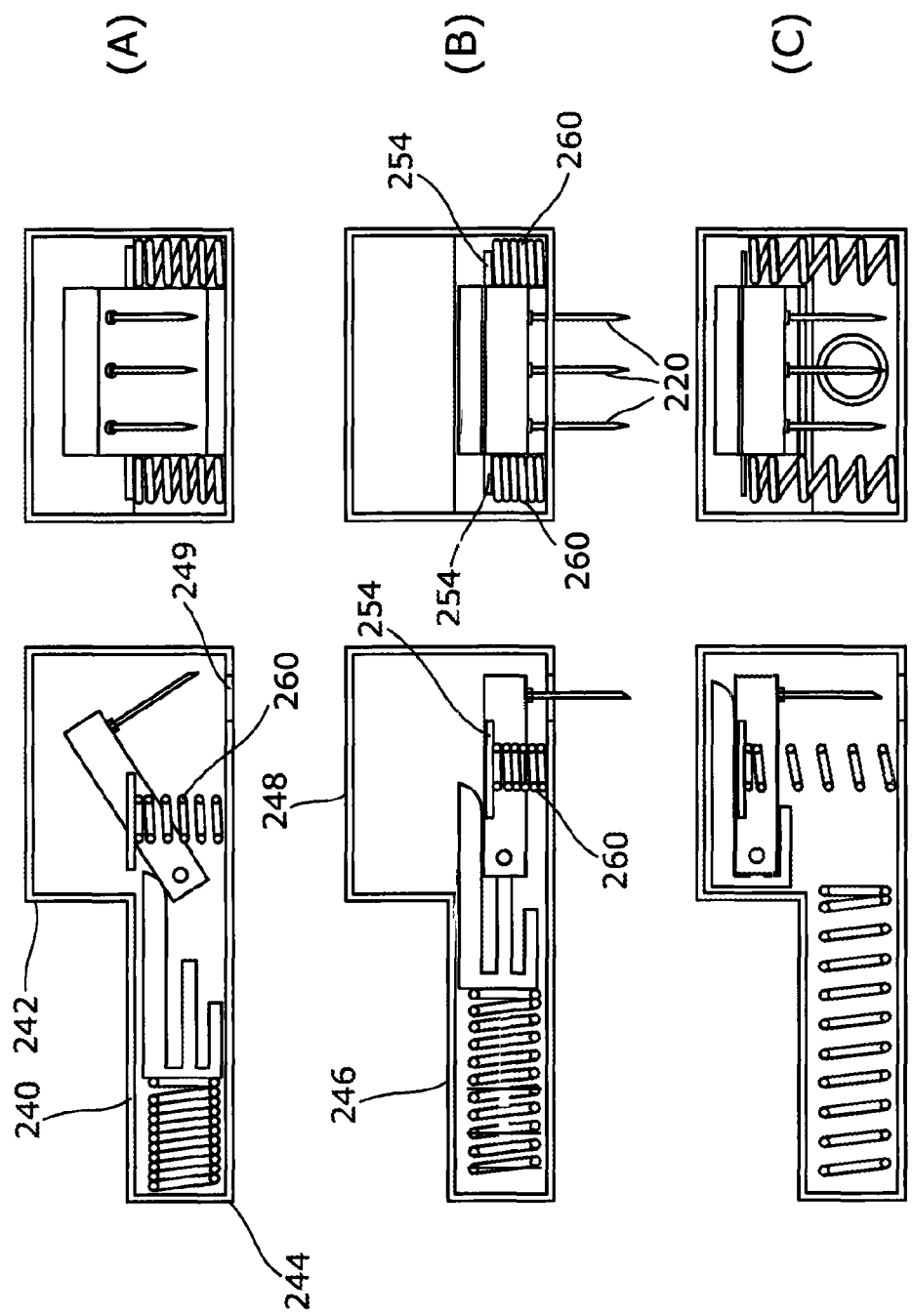
FIG. 2 schematically represents the actuation sequence of an injection device similar to that of the embodiment of FIG. 1 but additionally including a retraction arrangement.

FIG. 2 shows a modified version of the embodiment of FIG. 1 in which the injection device is also arranged to retract the needles 220 after completion of an injection. This may be particularly useful in eliminating additional steps to be carried out by a user at completion, particularly given that the device may be worn for a prolonged period of time.

In the embodiment of FIG. 2, the drive member 234 is releasable coupled to the spring 234 but is initially restrained within a track 246 which prevents transverse movement of the drive member 234. The track may be formed by the shape of the housing as shown or alternatively may be defined by interconnecting features of the drive member and housing. A pair of biasing springs 260 are provided between the housing 240 and a portion 254 of the carrier 250. Initially the springs 260 bias the carrier away from the delivery position. The drive member 234 initially compresses the springs 260 as it cams the carrier 250 downward but upon completion of the delivery sequence the drive member 234 has passed outside of the narrow track portion 246 of the housing 244. Thus, as shown in FIG. 2(C) the springs 260 are able to move the carrier 250 and drive member 234 transversely upwardly in the expanded portion of the housing 248 such that the needles 220 are withdrawn.

Figure 3:
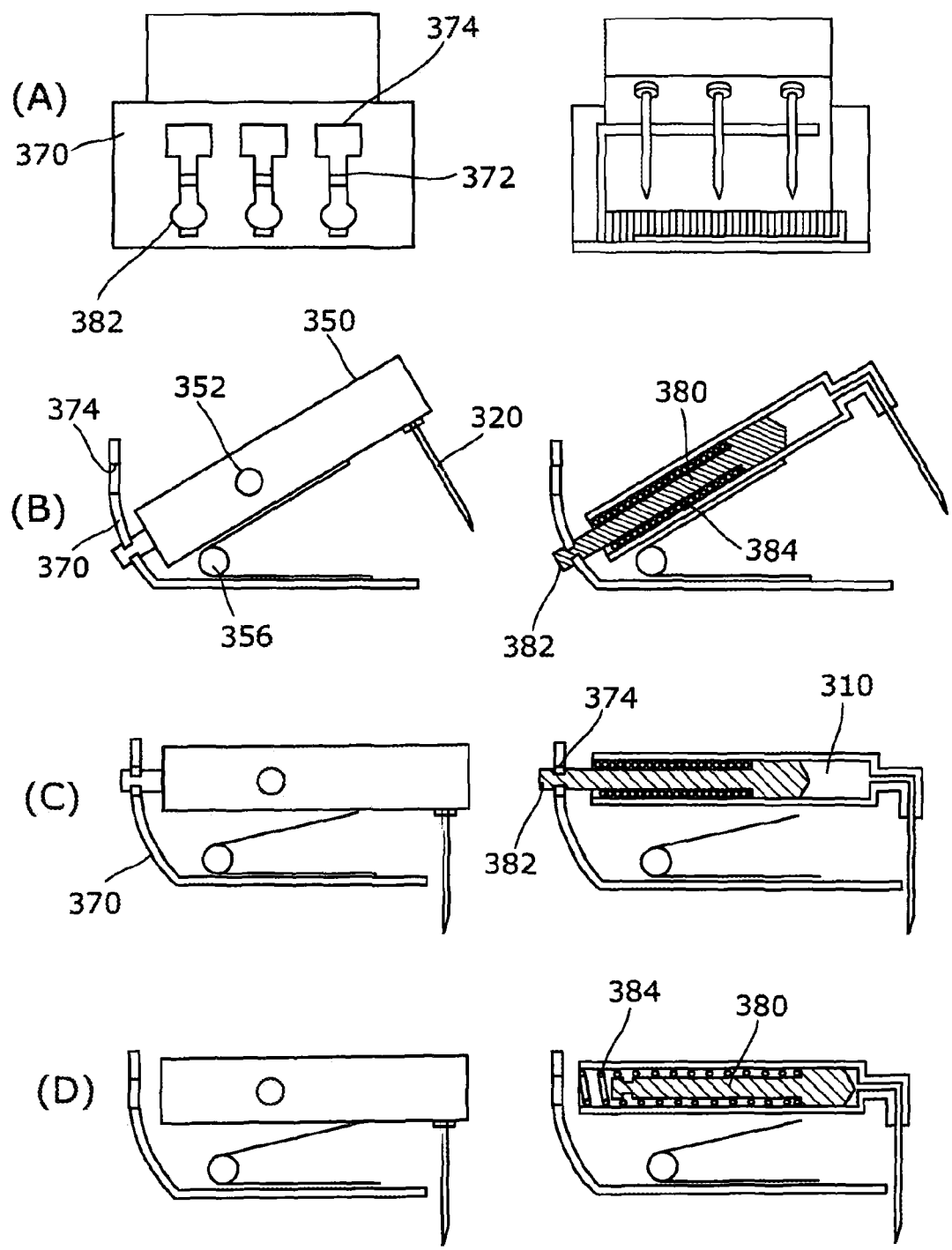
FIG. 3 schematically represents the actuation sequence of an injection device according to a further embodiment of the invention in profile and partial cut away.

A further embodiment is shown in FIG. 3 in which the carrier 350 is rotated between an initial position (FIG. 3(A)) and a delivery position (FIG. 3(C)) about a pivot 352. The carrier 350 may be latched in the initial position (for example by an activation trigger) against a stored energy device in the form of a torsion spring 356.

In this embodiment a plunger 380 is provided with a firing spring 384 which is provided within the cartridge 310 and is arranged to urge the plunger forward (against the cartridge cylinder) when released. The rearward end of the plunger is provided with a profiled head 382. A curved latch plate 370 is provided at the rear of the carrier 350 and is fixed relative to the device housing (not shown for clarity). The latch plate 370 is provided with a slot 372 which receives and restrains the profiled head 382 of the plunger 380. An opening in the form of a keyway 374 is provided at the end of the slot and is aligned with the delivery position of the carrier 350. Upon movement of the carrier 350 the head 382 of the plunger is translated along the slot 370 until it reaches the key way 374 (FIG. 3(C)). In this position the plunger is released and can travel forwards under the force of the spring 384 as shown in FIG. 3(D).

Figure 4:
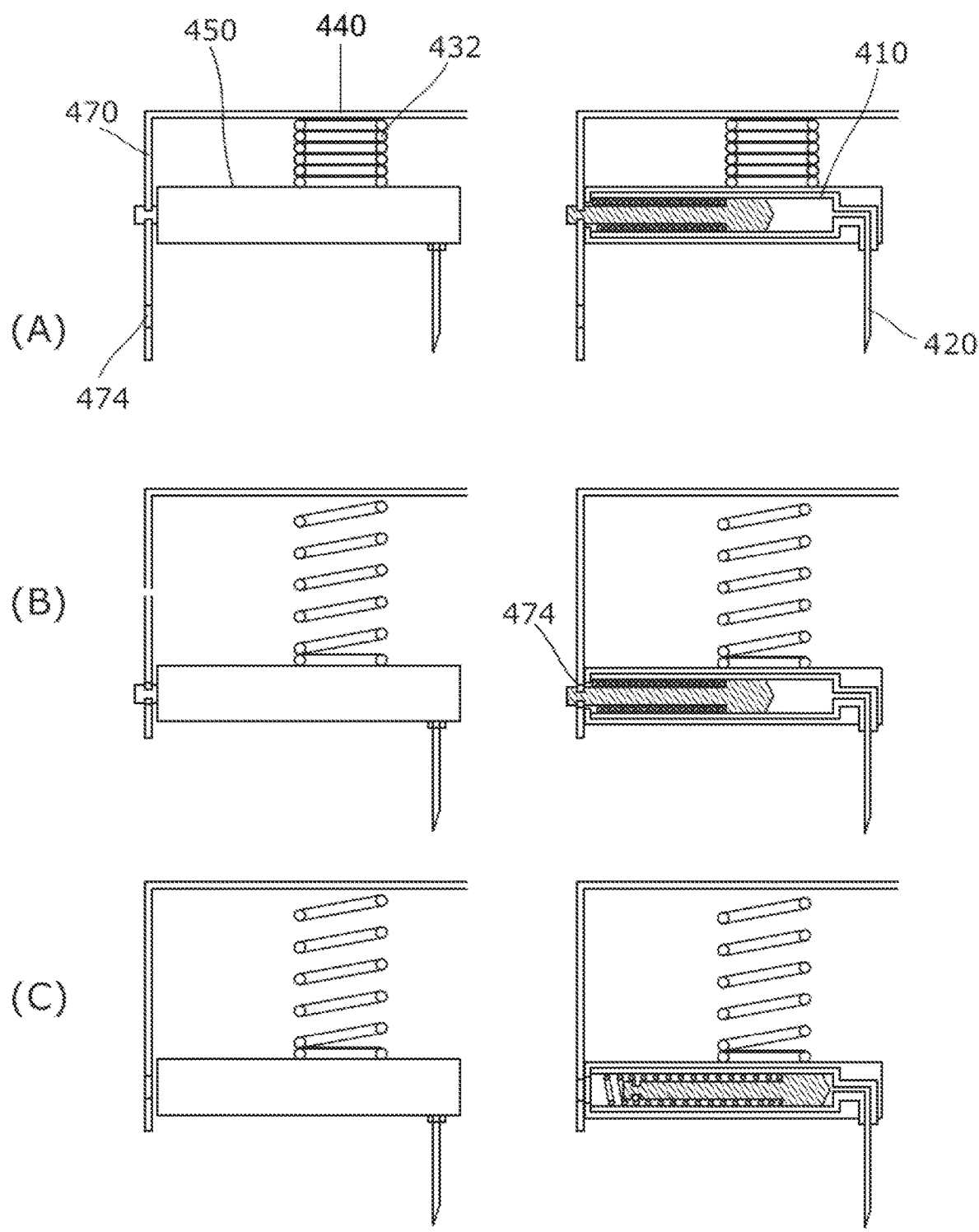
FIG. 4 schematically represents the actuation sequence of an injection device according to a further embodiment of the invention in profile and partial cut away.

The embodiment of FIG. 4 operates in a similar manner to the embodiment of FIG. 3 but uses a linear movement of the carrier 450. A compression spring 432 is provided between the housing 440 and the carrier 450 and, when released, urges the carrier 450, cartridge(s) 410 and needle(s) 420 downwardly to provide an insertion action of the needle. A latch plate 470 is provided including a slot and a keyway 474 aligned with the delivery position (FIG. 4(C)). The latch plate extends transversely and substantially perpendicular to the longitudinal axis of the injection device (but as with the embodiment of FIG. 3 the plunger, when released, is urged in the longitudinal direction).

Figure 5:
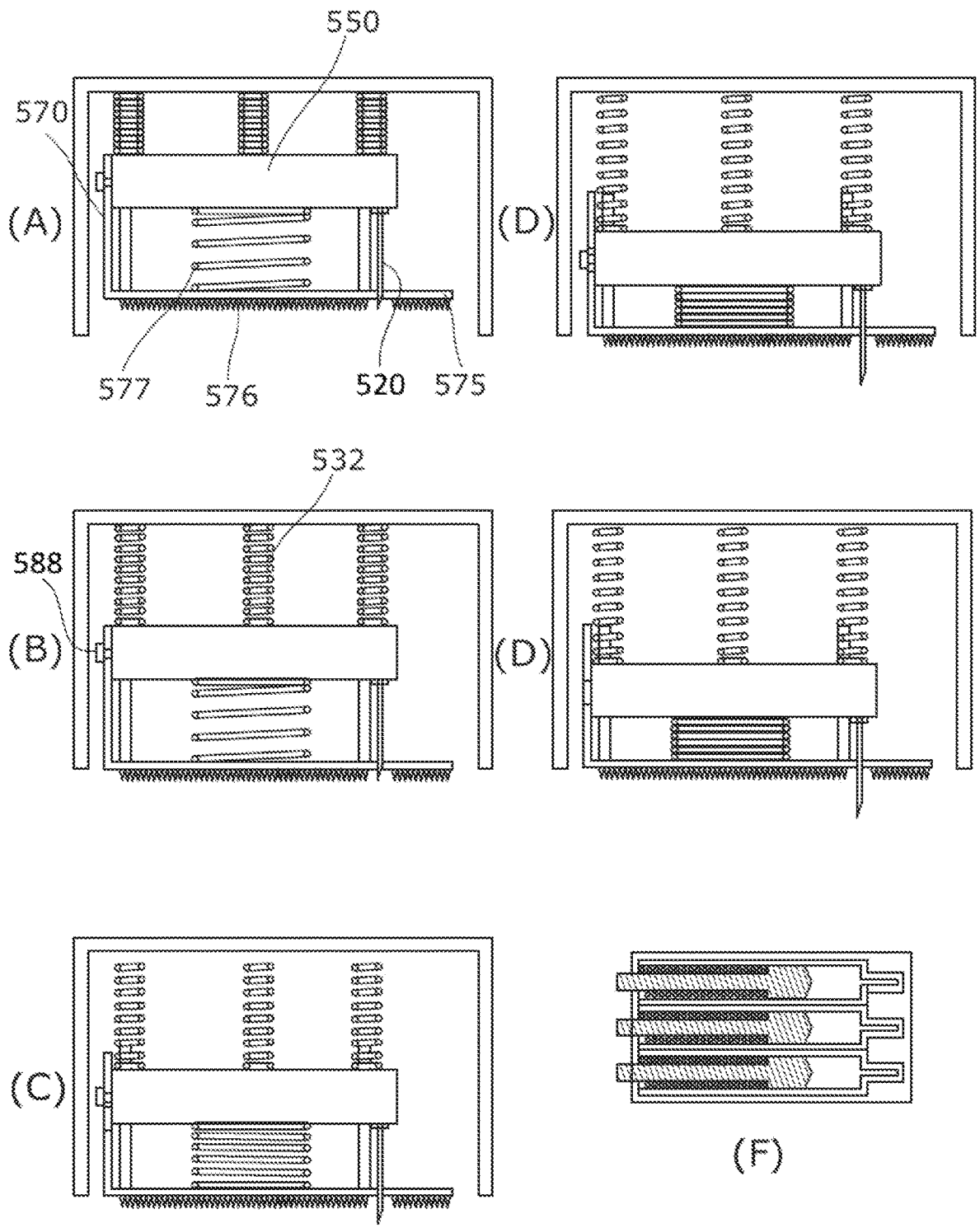
FIG. 5 schematically represents the actuation sequence of an injection device similar to that of FIG. 4 but further including a skin stimulates plate.
Figure 6:
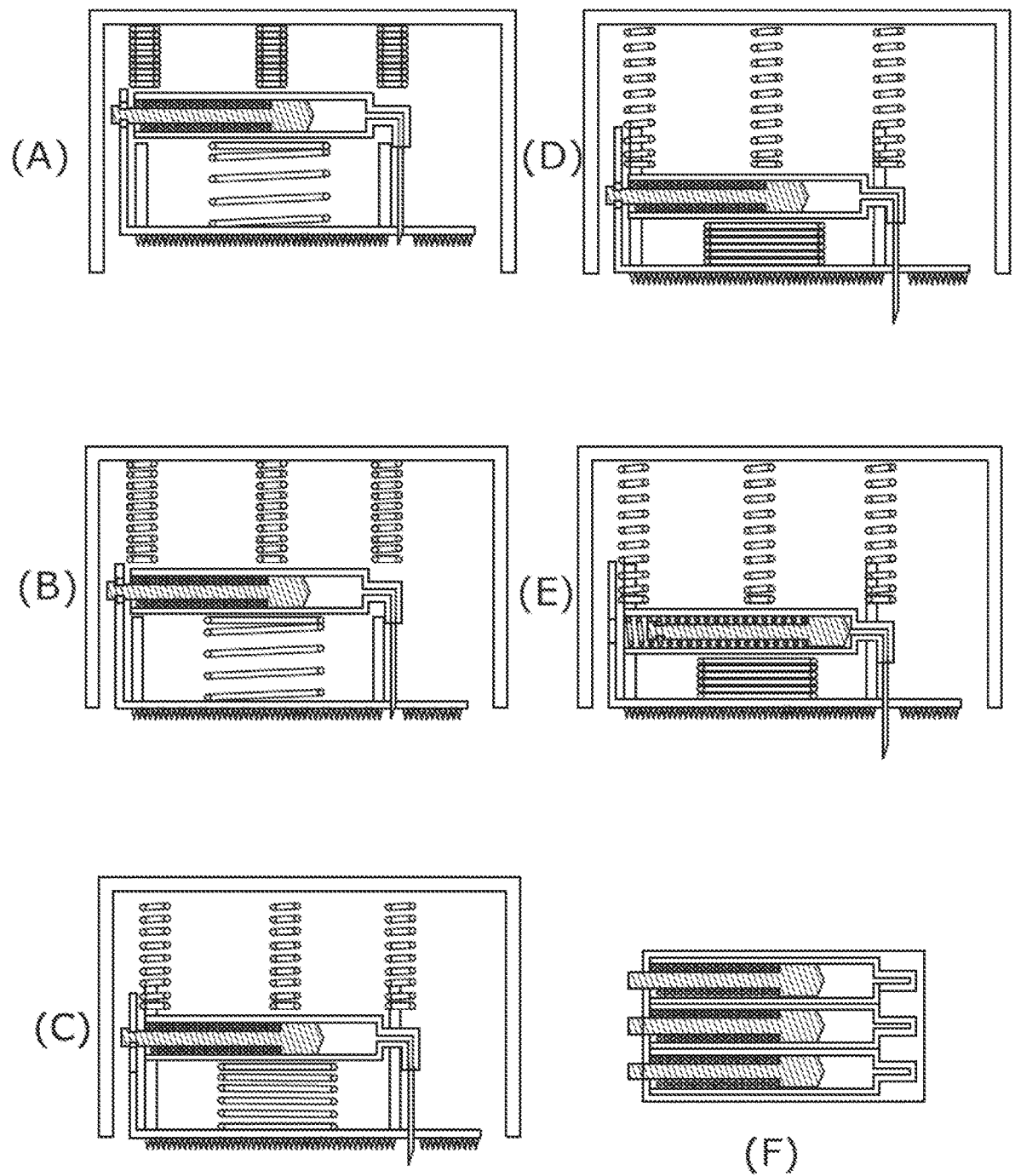
FIG. 6 is a partial cut away version of the embodiment of FIG. 5.

An alternative embodiment is shown in FIGS. 5 and 6 which further comprises a plate 575 which is coupled to the carrier 550 and is provided with skin stimuli in the form of an array of blunt spikes 576. The spikes are designed to stimulate the nerves in the skin but are not sharp or hard enough to penetrate or cause pain. The plate is moveably attached to the carrier 550 by a compression spring 577 which biases the plate downwardly (toward the skin in use) relative to the carrier 550. In the initial position of FIGS. 5(A) and 6(A) the spikes 576 of the plate 570 are spaced away from the lower plane of the housing so as to not be in contact with the skin of the user. The latch plate 570 is connected to the plate 575.

Figure 7:
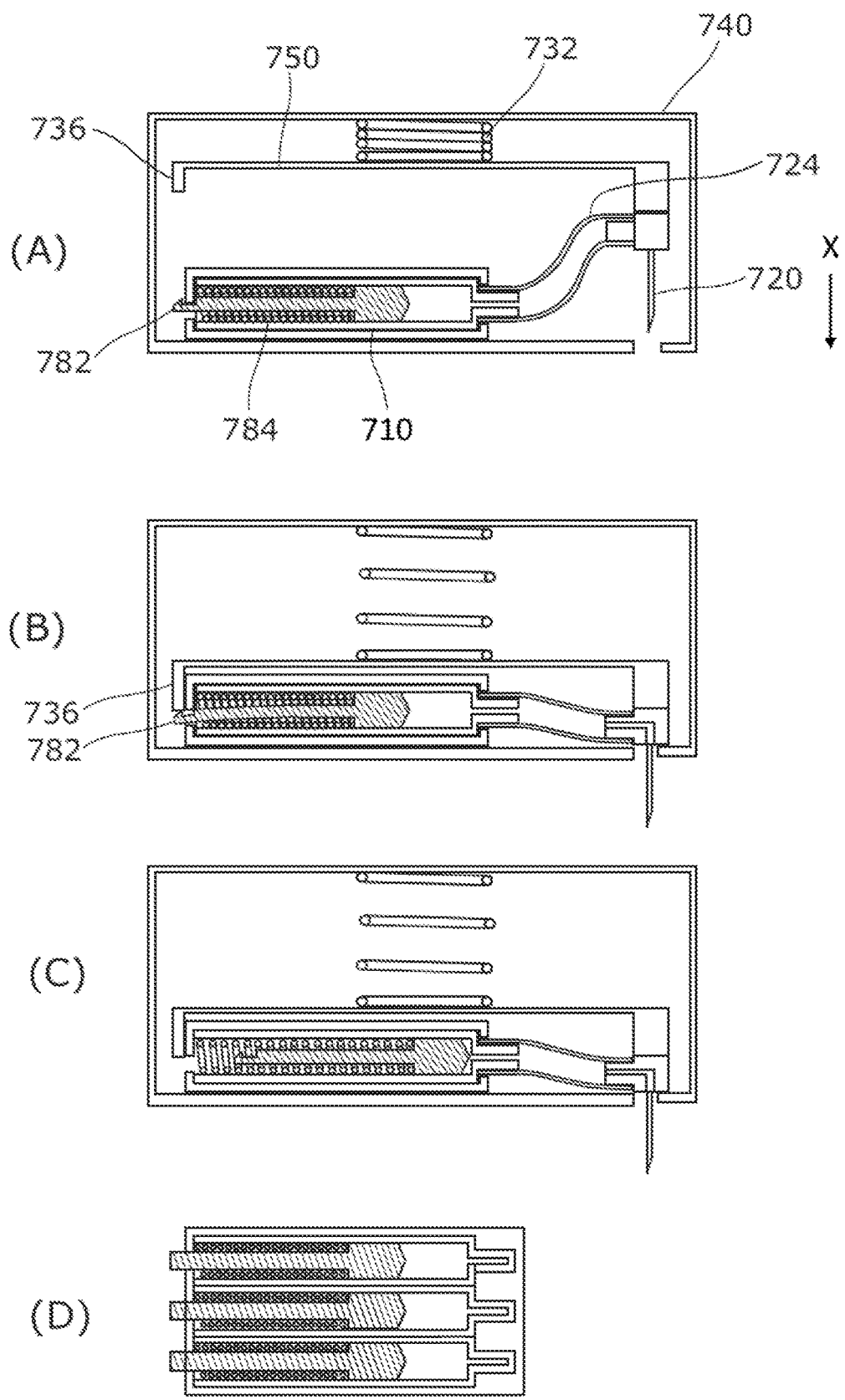
FIG. 7 schematically represents the actuation sequence of an injection device according to a further embodiment of the invention.

When the drive spring 532 is released the plate 575 and carrier 550 are initially driven together towards the skin (FIGS. 5(B) and 6(B)). When the plate contacts the skin the array of spikes introduce a sudden wide area stimuli to the skin. The forward movement of the plate 575 is halted by the skin contact and the drive spring 532 continues to urge the carrier 550 forward such that the needle(s) 520 pass beyond the plate 575 and penetrate the skin immediately after the contact of the skin stimuli. Thus, the sequencing of the device enables the pain of the needle 520 insertion to be masked (by "gate theory"). As the carrier 550 continues forward relative to the plate 575 the spring 577 is compressed allowing a degree of lost motion between the plate 575 and carrier 550. This enables the carrier 550 to move relative to the latch plate 570 to release the head of the plunger 588 in the same manner as the preceding embodiments to allow the spring An alternative embodiment shown in FIG. 7 uses a cartridge which is fixed relative to the housing 740, The drive mechanism of this embodiment includes a coil spring 732 which drives a carrier 750 which carries the plurality of needles 720 transversely and downwardly relative to the housing in the direction labelled X such that the needle projects beyond the lower plane of the housing in a delivery position (FIG. 7(B)). At least one flexible conduit 724 is provided between the needle 720 and cartridge 710 to enable the relative movement therebetween during the insertion movement. Typically, one conduit 724 may be provided for each needle 720 and a corresponding cartridge 710 (although it will be appreciated that alternatively a single conduit could be combined with a manifold to distribute the medicament between the needles and/or from the cartridges). The carrier 750 further includes a trigger member 736 which is arranged to unlatch the profiled head 782 from a latch at the rear of the cartridge 710 to enable the springs 784 to drive the cylinder forward and dispense the medicament. As can be seen in FIGS. 7(B) and (C) the sequencing of the delivery mechanism is arranged such that the trigger member 736 only engages the plunger end/profiled head 782 once the needle is fully in the delivery position. The plunger end/profiled head 782 is resiliently deflected to release the plunger.

Figure 8:
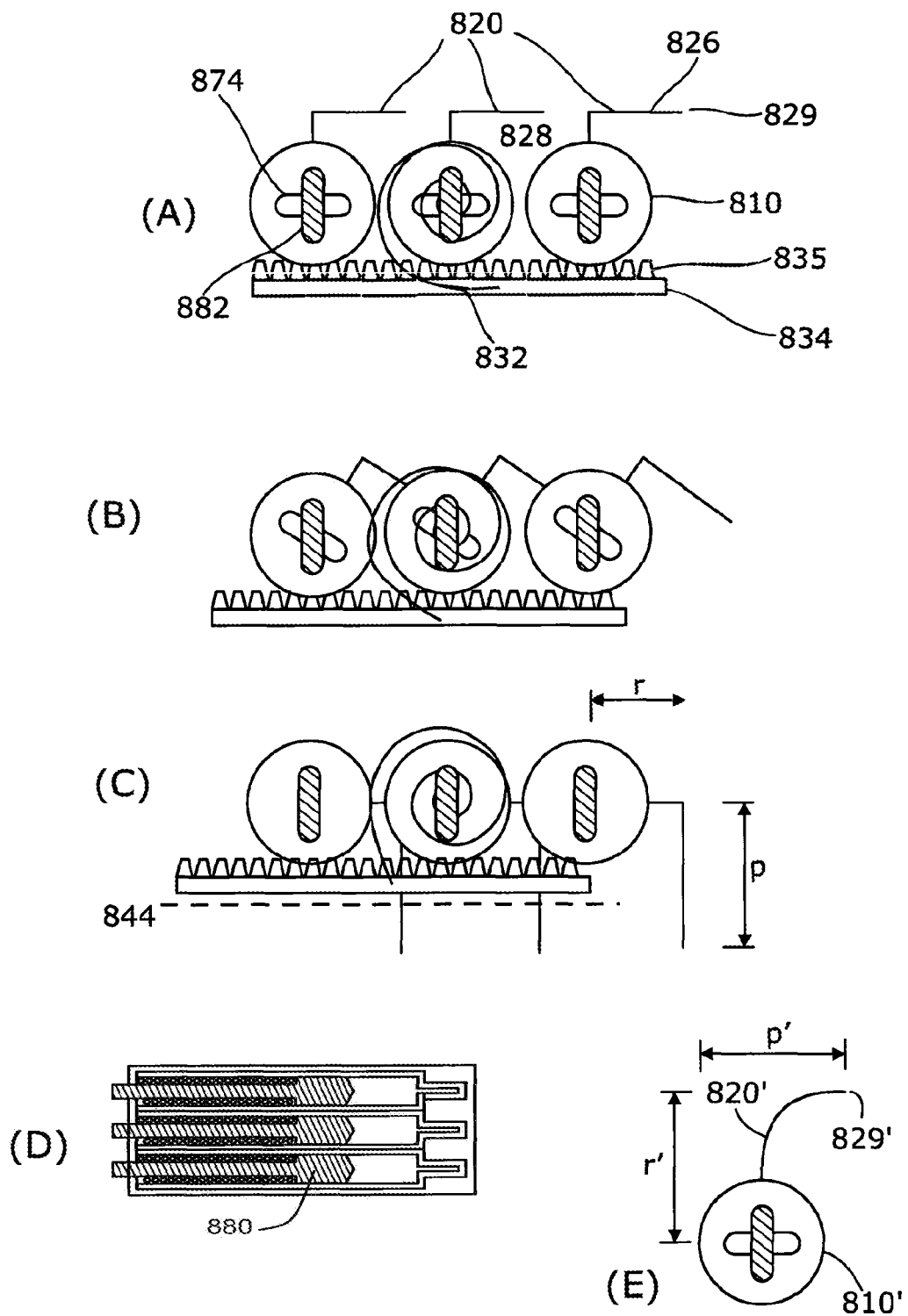
FIG. 8 schematically represents the actuation sequence of an injection device according to a further embodiment of the invention.

A further embodiment, shown in FIG. 8 utilises a rotation of the cartridges 810 about their longitudinal axis to both insert the needles 820 and release the plungers 880 for longitudinal movement under the bias of drive springs 884. This embodiment may provide a particularly low profile injector in the transverse direction extending away from the users skin in use. The needle 820 has a tip 829 which is radially offset from the longitudinal axis of the cartridge (by a distance r) and extends forwardly in the radial plane in a direction perpendicular to the radial direction of the offset (by a direction p). Whilst the figures show the needle 820 having a perpendicular angled intersection between the radial section 828 and the forwardly projecting section 826 it will be appreciated that the needle 820' may equally have an arcuate profile as shown in FIG. 8(E) (and the arc shape may be tailored to aid the penetration path of the needle). Equally, it will be appreciated that whilst the radial section 828 is illustrated as part of the needle 820 in the figures it could alternatively be a conduit associated with the needle 810 (such that the needle could extend only in the forward (perpendicular) direction).

The delivery mechanism of this embodiment comprises a stored energy device in the form of a constant force spring 832 which is arrange to rotate at least one of the cartridges 810 (although it will be appreciated that alternatively forms of spring may be used—for example by indirectly rotating the cartridge via a separate drive component). To enable a plurality of side-by-side cartridges to be rotated simultaneously the drive mechanism further comprises a linearly moveable plate 834 which is coupled to the outer surface of each cartridge 810. Any suitable complimentary engagement features may be provided between the plate 834 and cartridges 810 but in the illustrated example the plate is provided with a toothed profile 835 which engages corresponding teeth (not shown) on the outer circumferential surface of the cartridges (acting as a rack and pinion type arrangement). When the spring 832 rotates the cartridge with which it is associated it engages and moves the plate 834 in a tangential tangential direction with respect to the outer surface of the cartridge. The other cartridges 810 are engaged by such movement of the plate 834 and rotate simultaneously and in the same direction as the driven cartridge. As the cartridges rotates the needles 820 are rotated about an offset radial axis (r) and following a 90 degree rotation the needles project downwardly beyond the lower plane 844 of the injector housing such that they may penetrate the skin of a user.

In a similar manner to earlier embodiments the plunger 880 associated with each syringe 820 is provided with a forward biasing drive spring 884 (which is within the cartridge 810) and a profiled head 882 of the plunger 880 is initially held in a latched position against the spring 884. The profiled head 882 is positioned in a keyway 874 associated with the cartridge 810 and in the initial position of FIG. 8(A) the keyway and head are rotationally misaligned. One of the keyway 874 and head 882 are rotationally fixed relative to the housing (in the illustrated example the plunger is rotationally fixed) whilst the other rotates with the cartridge 810. Thus, when the delivery mechanism reaches the delivery position of FIG. 8(C) the keyway 874 and head 882 are aligned allowing the plunger to be urged forwardly by the spring 884 so as to dispense the medicament from the cartridge via the needles 810.

Although the invention has been described above with reference to one or more preferred embodiments, it will be appreciated that various changes or modifications may be made without departing from the scope of the invention as defined in the appended claims. For example, whilst the needles in the illustrated examples are generally illustrated having straight profiles it will be appreciated that they may have curved or transitioned profiles (for example to assist with insertion into the skin in those embodiments in which the needle is rotated into the delivery position).

The invention claimed is:

1. An injection device, comprising:
   a housing for at least one cartridge containing a medicament to be administered to a patient;
   at least one needle mounted within the housing and extending, in a direction which is non-parallel to a longitudinal axis of the at least one cartridge, from a rear end of the at least one needle associated with the at least one cartridge, to a tip of the at least one needle, wherein the at least one needle is moveable relative to the housing between a retracted position and a delivery position in which the tip of the at least one needle is displaced by a distance in a direction transverse to the housing; and
   a delivery mechanism configured to move the at least one needle between the retracted position and the delivery position and to dispense the medicament from the at least one cartridge, the delivery mechanism comprising:
   a coil spring releasable to urge the at least one needle from the retracted position to the delivery position;
   a plunger having a forward end extending into the at least one cartridge for expressing a dose in use, and a rearward end including a profiled head;
   a biasing element arranged to urge the plunger in a direction parallel to the longitudinal axis of the at least one cartridge toward a forward position;
   a latch fixed relative to the housing and arranged to receive the profiled head of the plunger and retain the plunger in a rearward position against an opposing force of the biasing element;
   wherein movement of the at least one needle to the delivery position releases the plunger from the latch such that the biasing element urges the plunger to the forward position;
   wherein the housing is configured to receive the at least one cartridge in a position fixed relative to the housing; and
   wherein the at least one needle is connected to the at least one cartridge by at least one flexible conduit in both the retracted position and the delivery position to allow relative movement between the at least one needle and the at least one cartridge.

2. The injection device of claim 1, wherein the delivery mechanism includes a trigger member arranged to resiliently deflect the profiled head of the plunger to release the plunger from the latch.

3. The injection device of claim 1, further comprising a plate having at least one skin stimulating member that is moveable relative to the housing.

4. The injection device of claim 3, wherein the delivery mechanism is arranged to move the plate into contact with the patient's skin prior to the at least one needle reaching the delivery position.

5. The injection device of claim 3, wherein the plate is compressibly mounted relative to the at least one needle.

6. The injection device of claim 1, wherein the injection device is configured to be worn, in use, against skin of the patient.

* * * * *